(12) United States Patent
Chung et al.

(10) Patent No.: US 9,095,851 B2
(45) Date of Patent: Aug. 4, 2015

(54) APPARATUS AND METHOD OF DETECTING AND CONTROLLING FLUID IN MICROFLUIDIC DEVICE

(71) Applicant: Samsung Electronics Co., Ltd., Suwon-si, Gyeonggi-do (KR)

(72) Inventors: Won-seok Chung, Suwon-si (KR); Kak Namkoong, Suwon-si (KR); Chin-sung Park, Seoul (KR); Kyung-ho Kim, Seoul (KR); Joon-ho Kim, Seongnam-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 172 days.

(21) Appl. No.: 13/722,057

(22) Filed: Dec. 20, 2012

(65) Prior Publication Data

US 2013/0306160 A1 Nov. 21, 2013

(30) Foreign Application Priority Data

May 18, 2012 (KR) .................. 10-2012-0053158

(51) Int. Cl.
*G01N 21/55* (2014.01)
*B01L 3/00* (2006.01)
*G01N 35/00* (2006.01)

(52) U.S. Cl.
CPC .... *B01L 3/502746* (2013.01); *G01N 35/00069* (2013.01)

(58) Field of Classification Search
CPC ............ B01L 3/502746; E21B 47/102; G01N 21/3504; G01N 21/3577; G01N 21/552
USPC ......... 356/445, 448, 132, 128, 134, 433, 436, 356/440, 442, 24; 250/573–576, 341.8, 250/339.11, 559.4, 573–576; 422/82.09; 436/46, 52
See application file for complete search history.

(56) References Cited

U.S. PATENT DOCUMENTS

| | | | |
|---|---|---|---|
| 4,197,459 A | 4/1980 | Perrem | |
| 4,547,070 A * | 10/1985 | Moll et al. | ..................... 356/339 |
| 5,017,775 A | 5/1991 | Granz et al. | |
| 5,071,248 A | 12/1991 | Tiefenthaler et al. | |
| 5,508,521 A | 4/1996 | Kraft et al. | |
| 5,684,296 A | 11/1997 | Hamblin et al. | |
| 5,864,391 A | 1/1999 | Hosokawa et al. | |
| 6,024,249 A | 2/2000 | On | |
| 6,750,468 B2 | 6/2004 | Malmstrom et al. | |
| 7,372,063 B2 | 5/2008 | Castro | |
| 7,879,619 B2 * | 2/2011 | Jing et al. | ..................... 436/171 |
| 2001/0024272 A1 | 9/2001 | Luetjens | |
| 2004/0109156 A1 * | 6/2004 | DiFoggio et al. | ............. 356/128 |
| 2008/0218746 A1 | 9/2008 | Castro | |
| 2008/0304082 A1 | 12/2008 | Gotz et al. | |
| 2010/0182605 A1 | 7/2010 | Stockwell et al. | |
| 2010/0200756 A1 | 8/2010 | Maiden | |

FOREIGN PATENT DOCUMENTS

| | | |
|---|---|---|
| JP | 11-125596 | 5/1999 |
| JP | 2004-317211 | 11/2004 |
| JP | 2004-340702 | 12/2004 |

* cited by examiner

*Primary Examiner* — Tri T Ton
(74) *Attorney, Agent, or Firm* — Leydig, Voit & Mayer, Ltd.

(57) ABSTRACT

A fluid control apparatus including a detecting unit including a light source for irradiating light toward a microfluidic device, and a photodetector for detecting light reflected from the microfluidic device, a transporting unit for moving the detecting unit; and a determining unit for controlling a transporting operation by the transporting unit, where determining a state of a fluid at a particular position relative to the microfluidic device is based on light reflected from the microfluidic device, and method of using same.

24 Claims, 8 Drawing Sheets

APPARATUS AND METHOD OF DETECTING AND CONTROLLING FLUID IN MICROFLUIDIC DEVICE

CROSS-REFERENCE TO RELATED APPLICATIONS

This application claims the benefit of Korean Patent Application No. 10-2012-0053158, filed on May 18, 2012, in the Korean Intellectual Property Office, the disclosure of which is incorporated by reference herein in its entirety.

BACKGROUND

1. Field

The present disclosure relates to methods and apparatuses for detecting and controlling a fluid in a microfluidic device. More particularly, the present disclosure relates to methods and apparatuses for rapidly and exactly determining whether a fluid at a particular position of a micro-channel in a microfluidic device is a liquid or a gas, and for controlling movement of the fluid in the microfluidic device based on the determination regarding the state of the fluid.

2. Description of the Related Art

According to developments in a personalized medical care, procedures such as genetic analysis, extrasomatic diagnosis, genetic nucleotide sequence analysis, and the like have become important, and the need for them has increased. Accordingly, a system capable of rapidly performing many tests by using a small sample amount is being developed and commercialized. Also, in order to embody the system, a microfluidic device, such as microfluidics or a lab-on-a-chip (LOC), is being highlighted. The microfluidic device including a plurality of micro-channels and a plurality of micro-chambers is designed to control and to handle a very small amount of fluid (e.g., a fluid in the range of about several nl (nanoliters) to about several ml (milliliters)). By using the microfluidic device, a reaction time of a microfluid may be minimally decreased, and reaction of the microfluid and measurement of a result thereof may be simultaneously performed. The microfluidic device may be manufactured by using various methods, and various materials are used according to the various methods.

The microfluidic device includes a plurality of micro-chambers in which reactions occur and a plurality of micro-channels for providing a sample or a reagent to the plurality of micro-chambers. Thus, in order to control movement of the sample or the reagent to a desired place, it is necessary to exactly detect a state of each micro-channel and a state of a fluid (i.e., liquid or gas) in the plurality of micro-channels. However, because a size of each micro-channel and a size of each micro-chamber of the microfluidic device are in the range of about several tens of µm (micrometers) to about several hundreds of µm, it is difficult to rapidly and exactly detect the state of the fluid.

Examples of currently proposed fluid detection methods include a method of disposing a plurality of electrodes in a micro-channel and then detecting a state of a fluid by measuring resistance variation between the electrodes, and a method of capturing an image of a portion of a micro-channel and then determining a state of a fluid via an image processing operation. In the case of the method of using electrodes, it is difficult to dispose the electrodes in the micro-channel, the manufacturing costs of a microfluidic device may increase, and there is a possibility that a sample or a reagent may be contaminated. In the case of the method of capturing an image, there is a spatial limit due to disposal of an image-capturing device and lighting, and a determination speed may be decreased due to the image processing operation.

SUMMARY

Provided are methods and apparatuses for determining whether a fluid at a particular position of a micro-channel in a microfluidic device is a liquid or a gas, and for controlling movement of the fluid in the microfluidic device based on the determination regarding the state of the fluid.

Additional aspects will be set forth in part in the description which follows and, in part, will be apparent from the description or may be learned by practice of the presented embodiments.

According to an aspect of the present disclosure, a fluid control apparatus includes a detecting unit configured to irradiate light towards a microfluidic device, detect light reflected from the microfluidic device, and output a signal based on the light reflected from the microfluidic device; a transporting unit configured to move the detecting unit to a measurement position relative to the microfluidic device; a determining unit configured to control a transporting operation performed by the transporting unit, and determine a state of a fluid in the microfluidic device at the measurement position based on the signal output from the detecting unit; and a fluid control unit configured to control movement of the fluid in the microfluidic device based on the state of the fluid determined by the determining unit, wherein the determining unit determines whether the fluid in the microfluidic device at the measurement position is a liquid or a gas based on the intensity of the light reflected from the microfluidic device.

The detecting unit may include a light source that irradiates light toward the microfluidic device, and a photodetector that detects the light reflected from the microfluidic device.

The detecting unit may further include a reflection plate that reflects light, which has passed through the microfluidic device, toward the photo detector.

The light source and the photodetector may be disposed opposite the reflection plate relative to the microfluidic device.

The transporting unit may include a frame; a motor that is disposed at a side of the frame; a lead screw that is rotated by the motor, a mount that performs linear movement according to rotation of the lead screw; and a guide bar that is attached to the frame so as to stably guide movement of the mount.

The light source and the photodetector may be disposed at the mount.

The mount may include a holder capable of sliding on the guide bar to guide the movement of the mount.

The transporting unit may further include one or more position sensors that are attached on the frame so as to detect a position of the mount while the mount moves.

The determining unit may include a sensor circuit for exchanging a signal with the detecting unit; a driving circuit for exchanging a signal with the transporting unit; a control circuit that controls the detecting unit via the sensor circuit and controls the transporting unit via the driving circuit; and control software that controls operations of the control circuit, and determines a state of a fluid based on a signal from the detecting unit.

The determining unit may determine the state of the fluid by comparing a value of the intensity of the reflected light, which is measured by the detecting unit, with a reference value.

The determining unit may determine the state of the fluid by comparing an average value of a plurality of pieces of data with a reference value, wherein the plurality of pieces of data include current data regarding the intensity of the reflected light, which is measured by the detecting unit, and a plurality of pieces of previous data regarding the intensity of the reflected light which is measured directly before the current data.

The determining unit may determine the state of the fluid by comparing a difference value with a reference value, wherein the difference value corresponds to a difference between an average value of a plurality of pieces of data regarding intensity of light which is most recently measured by the detecting unit and an average value of a plurality of pieces of previous data regarding the intensity of the light which was previously measured a predetermined number of times.

The determining unit may determine the state of the fluid by comparing a differential value with a reference value, wherein the differential value is obtained by using intensity of light which is most recently measured by the detecting unit and the intensity of the light which was previously measured a predetermined number of times.

The determining unit may determine the state of the fluid by comparing a differential value with a reference value, wherein the differential value is obtained by using an average value of a plurality of pieces of data regarding intensity of light which is most recently measured by the detecting unit and an average value of a plurality of pieces of previous data regarding the intensity of the light which was previously measured a predetermined number of times.

The determining unit may finally determine a change in the state of the fluid after a signal indicating the change in the state of the fluid is continuously shown over a predetermined number of times.

According to another aspect of the present disclosure, a method of controlling a fluid includes operations of moving a light source and a photodetector to a measurement position relative to a microfluidic device; irradiating light towards the microfluidic device; measuring an intensity of light reflected from the microfluidic device; determining whether a state of a fluid in the microfluidic device is changed from a gas state to a liquid state or is changed from a liquid state to a gas state based on a change in the measured intensity of the light reflected from the microfluidic device; and controlling movement of the fluid in the microfluidic device based on the state of the fluid in the microfluidic device.

The determining operation may include an operation of determining the state of the fluid by comparing the measured intensity of the reflected light with a reference value.

The determining operation may include an operation of determining the state of the fluid by comparing an average value of a plurality of pieces of data with a reference value, wherein the plurality of pieces of data include current data regarding the measured intensity of the reflected light, and a plurality of pieces of previous data regarding the intensity of the reflected light which is measured directly before the current data.

The determining operation may include an operation of determining the state of the fluid by comparing a difference value with a reference value, wherein the difference value corresponds to a difference between an average value of a plurality of pieces of data regarding intensity of light which is most recently measured and an average value of a plurality of pieces of previous data regarding the intensity of the light which was previously measured a predetermined number of times.

The determining operation may include an operation of determining the state of the fluid by comparing a differential value with a reference value, wherein the differential value is obtained by using intensity of light which is most recently measured and the intensity of the light which was previously measured a predetermined number of times.

The determining operation may include an operation of determining the state of the fluid by comparing a differential value with a reference value, wherein the differential value is obtained by using an average value of a plurality of pieces of data regarding intensity of light which is most recently measured and an average value of a plurality of pieces of previous data regarding the intensity of the light which is previously measured a predetermined number of times.

The determining operation may include an operation of finally determining a change in the state of the fluid after a signal indicating the change in the state of the fluid is continuously shown over a predetermined number of times.

The method may further include an operation of moving the light source and the photodetector to a next measurement point after monitoring the state of the fluid at a current measurement position.

When a change in a state of a fluid is monitored at a measurement point, the determining operation may include an operation of determining that the state of the fluid is changed only at the measurement point.

When a change in a state of a fluid is monitored at all of a plurality of measurement points after scanning the plurality of measurement points in a section in which the fluid flows, the determining operation may include an operation of determining that the state of the fluid in the section is changed.

The method may further include operations of monitoring a state of a fluid at an initial measurement point after completing monitoring of the state of the fluid at all measurement points, and determining the state of the fluid at a current measurement point by comparing a previous measurement result with a current measurement result at the current measurement point.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
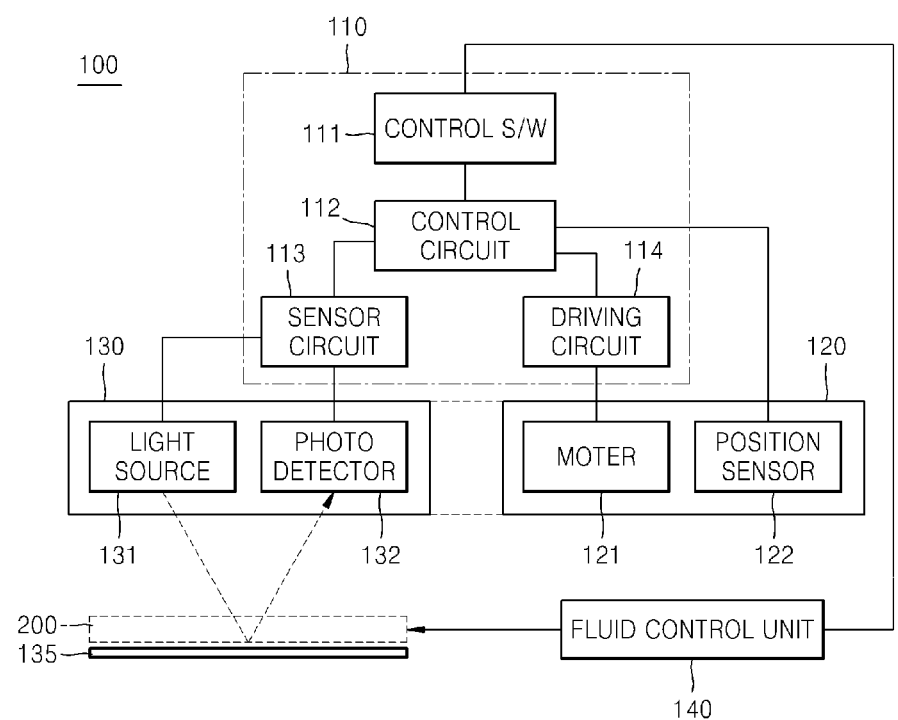
FIG. 1 is a block diagram illustrating a configuration of a fluid control apparatus, according to an example embodiment.

Reference will now be made in detail to embodiments of methods and apparatuses for detecting and controlling a fluid in a microfluidic device, examples of which are illustrated in the accompanying drawings. In the drawings, like reference numerals denote like elements, and the size of each component may be exaggerated for clarity.

FIG. 1 is a block diagram illustrating a configuration of a fluid control apparatus 100, according to an example embodiment.

Referring to FIG. 1, the fluid control apparatus 100 may include a detecting unit 130, a transporting unit 120, a determining unit 110, and a fluid control unit 140. The detecting unit 130 irradiates light toward a microfluidic device 200, detects the light reflected from the microfluidic device 200, and then outputs a signal. The transporting unit 120 moves the detecting unit 130 to a particular position relative to the microfluidic device 200. The determining unit 110 controls a transporting operation by the transporting unit 120 and determines a state of a fluid (i.e., liquid or gas) at the particular position of the microfluidic device 200 by referring to the signal measured by the detecting unit 130. The fluid control unit 140 controls movement of the fluid in the microfluidic device 200 based on the determination by the determining unit 110.

The detecting unit 130 may include a light source 131 for irradiating light toward the microfluidic device 200 and a photodetector 132 for detecting the light reflected from the microfluidic device 200. Examples of the light source 131 may include a light-emitting diode (LED) or a laser diode (LD). An example of the photodetector 132 may include a photo diode. In some embodiments, in order to simultaneously detect a state of a fluid at a plurality of positions in the microfluidic device 200, the detecting unit 130 may include an array of a plurality of the light sources 131 and a plurality of the photo detectors 132.

Because the microfluidic device 200 is generally formed of a transparent material, the microfluidic device 200 may transmit most of the light irradiated from the light source 131. In this case, the amount of light that is received by the photo detectors 132 may not be sufficient. Thus, in order to allow light that has passed through the microfluidic device 200 to be reflected toward the photodetector 132, the detecting unit 130 may further include a reflection plate 135 that is arranged at a bottom surface of the microfluidic device 200. The reflection plate 135 may be disposed opposite the light source 131 and the photodetector 132 relative to the microfluidic device 200. However, in embodiments where the bottom surface of the microfluidic device 200 has sufficient reflectivity, the reflection plate 135 may not be used.

In one embodiment, the transporting unit 120 is combined with the detecting unit 130 and functions to move the light source 131 and the photodetector 132 of the detecting unit 130 to a desired position relative to the microfluidic device 200. For example, the transporting unit 120 may move the light source 131 and the photodetector 132 to a particular position and then may stop at the particular position, or may repeatedly reciprocate the light source 131 and the photodetector 132 in a particular section. In order to perform the aforementioned operations, the transporting unit 120 may include a motor 121, a position sensor 122, and other driving members.

The determining unit 110 may control the transporting operation by the transporting unit 120 and a detecting operation by the detecting unit 130, and may determine a state of a fluid at a particular position of the microfluidic device 200. For example, the determining unit 110 may include a sensor circuit 113 that is connected to the detecting unit 130 and exchanges a signal with the detecting unit 130, a driving circuit 114 that is connected to the transporting unit 120 and exchanges a signal with the transporting unit 120, and a control circuit 112 that controls the sensor circuit 113 and the driving circuit 114 in response to a command from control software 111. The determining unit 110 may switch the light source 131 on/off and adjust the intensity of light emitted from the light source 131 by using the sensor circuit 113, may move the light source 131 and the photodetector 132 to a desired position, and may adjust a movement speed of the detecting unit 130 by controlling the transporting unit 120 via the driving circuit 114. The control software 111 may calculate positions of the light source 131 and the photodetector 132, and may determine a state of a fluid based on a signal from the photodetector 132 by, for example, using the method to be described below.

The fluid control unit 140 controls movement of a fluid in the microfluidic device 200, based on the determination by the determining unit 110. Although not illustrated in FIG. 1, a plurality of micro-channels in which a fluid such as a sample or a reagent flows, a plurality of micro-chambers in which a reaction between the sample and the reagent occurs, a plurality of micro-valves that control a flow of the fluid in the plurality of micro-channels, and a plurality of openings that are connected to the plurality of micro-channels and the plurality of micro-valves, respectively, are formed in the microfluidic device 200. For example, the fluid control unit 140 may include a plurality of pumps (not shown) that apply a vacuum or a pneumatic pressure to the plurality of micro-channels or the plurality of micro-valves via the plurality of openings. Since the plurality of pumps apply the vacuum or the pneumatic pressure to the plurality of micro-channels or the plurality of micro-valves via the plurality of openings, the fluid control unit 140 may push or draw the fluid in each of the plurality of micro-channels or may open and close the plurality of micro-valves. The fluid control unit 140 may control an operation of each of the plurality of pumps based on the determination by the determining unit 110 with respect to a state of a fluid in each of the plurality of micro-channels, so that the fluid control unit 140 may move a fluid in the microfluidic device 200 to a desired position.

Figure 2:
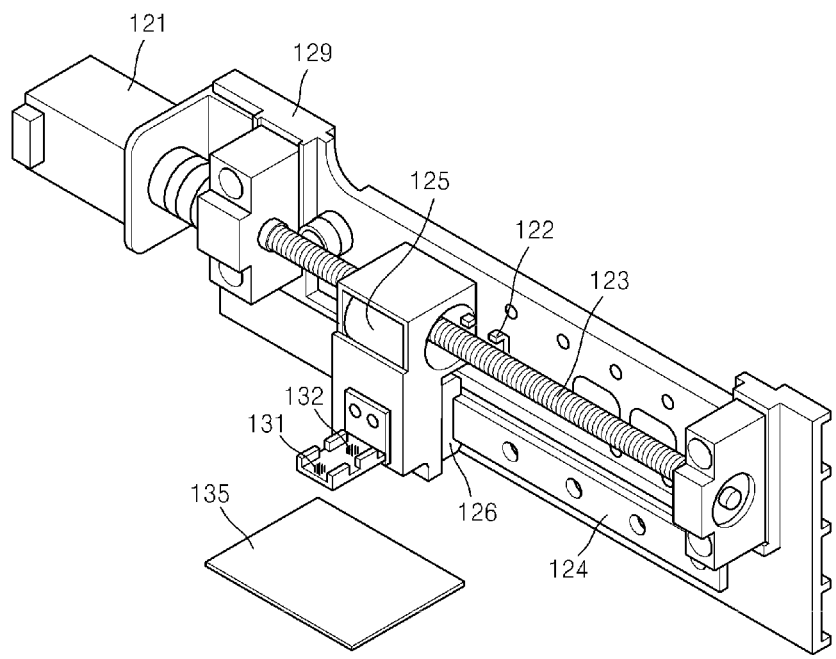
FIG. 2 is a perspective view illustrating a structure of a transporting unit of the fluid control apparatus, according to an example embodiment.

FIG. 2 is a perspective view illustrating a structure of the transporting unit 120 of the fluid control apparatus 100, according to an example embodiment.

Referring to FIG. 2, the transporting unit 120 may include a frame 129, the motor 121 that is disposed at a side of the frame 129, a lead screw 123 that is rotated by the motor 121, a mount 125 that performs linear movement according to the rotation of the lead screw 123, and a guide bar 124 that is attached to the frame 129 so as to stably guide movement of the mount 125. Each of the light source 131 and the photodetector 132 may be disposed at the mount 125 in a direction toward the reflection plate 135. Also, in some embodiments, a holder 126 that is configured to slide on the guide bar 124 to guide the movement of the mount 125 may be further combined with the mount 125. Also, the transporting unit 120 may further include one or more position sensors 122 to detect a position of the mount 125 while the mount 125 moves. For example, a plurality of position sensors 122 that are arrayed along a movement direction of the mount 125 may be attached on an inner wall of the frame 129. Referring to FIG.

2, one light source 131 and one photodetector 132 are disposed at the mount 125, but, as described above, in other embodiments, a plurality of the light sources 131 and/or a plurality of the photo detectors 132 may be disposed at the mount 125. In the structure of the transporting unit 120, while the mount 125 moves leftward and rightward according to a rotation direction of the motor 121, the mount 125 may dispose the light source 131 and the photodetector 132 at a particular position relative to the microfluidic device 200. Although not illustrated, by moving the frame 129 forward and backward, the light source 131 and the photodetector 132 may be two-dimensionally moved.

Figure 3:
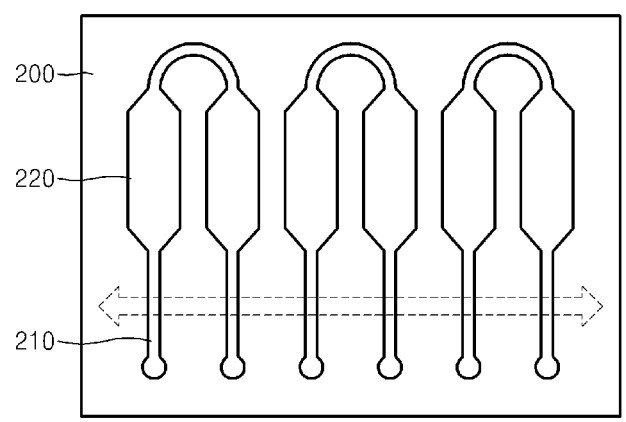
FIG. 3 is a plane view illustrating an example structure of a microfluidic device.

FIG. 3 is a plane view illustrating an example structure of the microfluidic device 200. As illustrated in FIG. 3, the microfluidic device 200 may include a plurality of micro-channels 210 in which a fluid such as a sample or a reagent flows, and a plurality of micro-chambers 220 in which a reaction between the sample and the reagent occurs. For example, the fluid control apparatus 100 may scan each of the plurality of micro-channels 210 of the microfluidic device 200 while the fluid control apparatus 100 moves the light source 131 and the photodetector 132 by using the transporting unit 120, so that the fluid control apparatus 100 may determine whether a liquid flows in the micro-channel 210 or a gas flows in the micro-channel 210.

Figure 4:
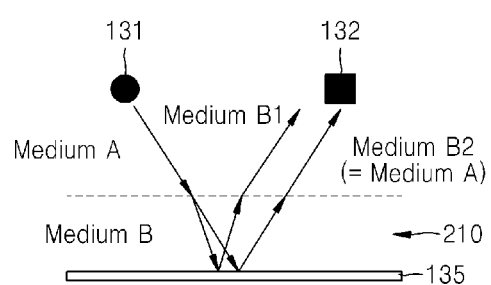
FIG. 4 is a conceptual view illustrating an operational principle of the fluid control apparatus, according to the example embodiment.

Hereinafter, a fluid state detecting operation by the fluid control apparatus 100 is described in detail. FIG. 4 is a conceptual view illustrating an operational principle of the fluid control apparatus 100, according to an example embodiment. Referring to FIG. 4, the light source 131 and the photodetector 132 are disposed to the same direction with respect to the microfluidic device 200, and the reflection plate 135 is disposed at the opposite direction of the light source 131 and the photodetector 132 with respect to the microfluidic device 200. It is assumed that there is a first medium A, such as, for example air, between the microfluidic device 200 and the light source 131 and the photodetector 132, and a second medium B flows in a micro-channel of the microfluidic device 200.

If the second medium B that flows in the micro-channel of the microfluidic device 200 is gas (for example, air) that is the same as the first medium A, light irradiated from the light source 131 is not refracted at an interface between the first medium A and the second medium B. However, in a case where the second medium B is changed to a liquid having a refractive index different from the first medium A, light is refracted at the interface between the first medium A and the second medium B, so that a travel path of the light is changed. As a result, an amount of the light that travels to the photodetector 132 is also changed, so that the fluid control apparatus 100 may detect a change of a material that flows in the micro-channel of the microfluidic device 200 by referring to a change in the amount of the light which is detected by the photodetector 132, e.g., the fluid control apparatus 100 may detect that the material is changed from a gas to a liquid or from a liquid to a gas.

Figure 5:
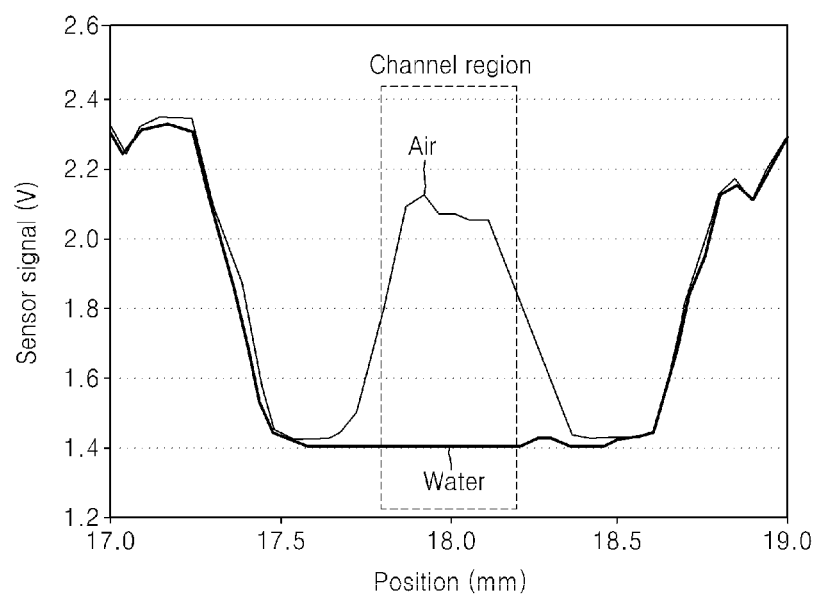
FIG. 5 is a graph illustrating an example of an optical signal obtained when the fluid control apparatus according to the example embodiment scans the microfluidic device.

FIG. 5 is a graph illustrating an example of an optical signal obtained when the fluid control apparatus 100 scans the microfluidic device 200, according to an example embodiment. The graph of FIG. 5 was obtained while the fluid control apparatus 100 moved around one micro-channel 210 of the microfluidic device 200 from a left side to a right side in a direction of an arrow shown in FIG. 3. In the example, the microfluidic device 200 was formed of polystyrene (PS), a depth of the micro-channel 210 was 300 μm, a width of the micro-channel 210 was 400 μm, and a laser having a center wavelength of 850 nm (nanometers) was used as the light source 131. Also, a reflection plate 135 comprising translucent silicon material was attached to a bottom surface of the micro-channel 210. Also, in the graph of FIG. 5, a part marked by a dotted box indicates a channel region of the micro-channel 210. Referring to FIG. 5, it is apparent that the optical signal is decreased when water flows in the micro-channel 210, compared to a case when air flows in the micro-channel 210. Thus, by selectively processing only data of coordinates that correspond to the region of the micro-channel 210, it is possible to easily determine whether a fluid in the micro-channel 210 is water or air. In this manner, by scanning the plurality of micro-channels 210 one by one, the fluid control apparatus 100 may control the plurality of micro-channels 210 in a parallel manner by using one light source 131 and one photodetector 132.

Figure 6:
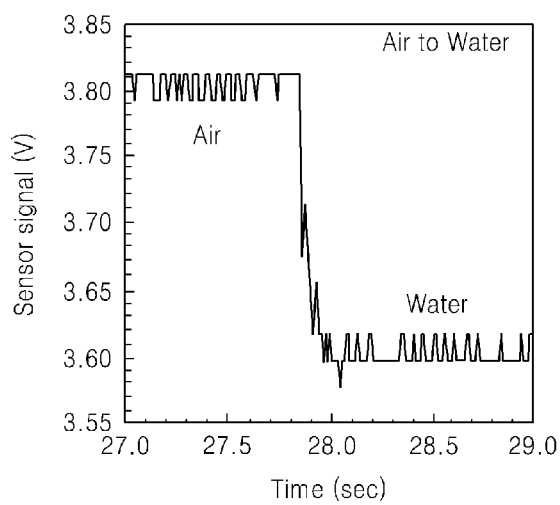
FIG. 6 is a graph illustrating variation of an optical signal according to a change in a state of a fluid in a micro-channel, according to an example embodiment.

FIG. 6 is a graph illustrating variation of an optical signal according to a change in a state of a fluid in the micro-channel 210, according to an example embodiment. The graph of FIG. 6 was obtained by measuring the variation of the optical signal when the fluid in the micro-channel 210 was changed from air to water. In the example shown in FIG. 6, a depth of the micro-channel 210 was 100 μm, a width of the micro-channel 210 was 400 μm, and a sampling rate was 100 Hz (hertz). Referring to FIG. 6, when the fluid in the micro-channel 210 was changed from air to water, the optical signal was decreased. Thus, by using this principle, while the fluid control apparatus 100 monitors a state of a fluid at a particular position of the microfluidic device 200, the fluid control apparatus 100 may detect a moment when a fluid in the micro-channel 210 is changed from gas to water or from water to gas, and may appropriately control the fluid in the microfluidic device 200 based on such information. For example, when intensity of light irradiated from the photodetector 132 is equal to or greater than a predetermined reference value, the control software 111 may determine that the fluid is a gas, and when the intensity of light irradiated from the photodetector 132 is less than the predetermined reference value, the control software 111 may determine that the fluid is a liquid.

Figure 7:
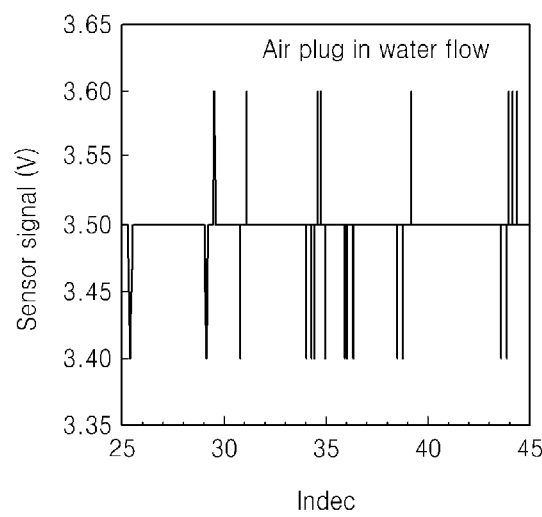
FIG. 7 is a graph illustrating variation of an optical signal when a liquid that flows in a micro-channel includes bubbles, according to an example embodiment.

However, as illustrated in FIG. 6, the optical signal exhibits an irregular noise component while the fluid is maintained in a constant state (i.e., either a liquid state or a gas state). In general, the noise component is incurred by droplets included in a gas or bubbles in a liquid. For example, FIG. 7 is a graph illustrating variation of an optical signal when a liquid (e.g., water) that flows in the micro-channel 210 includes bubbles. Due to the noise component, it may be difficult to exactly determine a point at which a state of the fluid is changed. Also, according to various factors including a size of a measurement point (e.g., the micro-channel 210), a distance between the measurement point and the light source 131 and the photodetector 132, a state of the reflection plate 135, and the like, a level of a difference between an optical signal when the fluid is water and an optical signal when the fluid is gas may be changed. Thus, when water that flows past the measurement point includes bubbles or air that flows past the measurement point includes droplets, a wrong determination may be arrived at before the state of the fluid is completely changed.

Descriptions will be provided below with respect to a determination algorithm for exactly determining a point of a fluid change, regardless of the aforementioned various factors.

Figure 8A:
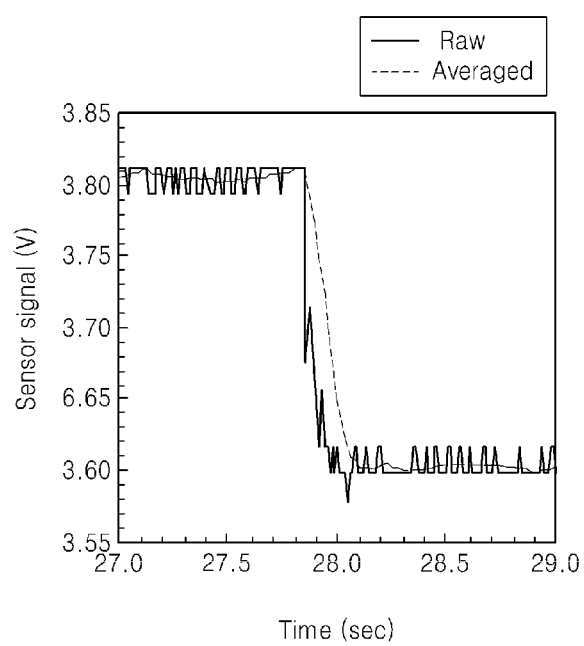
FIGS. 8A and 8B are graphs illustrating results of processing an optical signal according to an algorithm for determination of a change in a state of a fluid in a micro-channel, according to an example embodiment.

First, in order to reduce an effect due to a noise component, a plurality of pieces of data may be averaged, for example, by comparing an average value of light intensities measured at two or more different time points to a reference value. For example, in FIG. 8A, a graph denoted by a thin dotted line indicates an average of 16 pieces of previous data with respect to a point of a graph of original data that is denoted by a bold solid line. As illustrated in FIG. 8A, when the averaging method is used, it is possible to see that the noise component is decreased. Then, by comparing a value of the average graph with a predetermined reference value, a state of a fluid may be determined. For example, the averaging method may be calculated by using Equation 1 below.

$$S_c \le S_{avg}(n) = \frac{\sum_{k=1}^{n_a} S([n-(k-1)])}{n_a} \quad \text{[Equation 1]}$$

That is, as expressed via Equation 1, by comparing a value of $S_{avg}(n)$ that is obtained by averaging $n_a$ pieces of data including current data, which are previously measured, with a predetermined reference value $S_c$, it is possible to determine whether a fluid in the current micro-channel 210 is a gas (e.g., air) or a liquid (e.g., water, a sample, or a reagent). Here, the reference value $S_c$ may be a predefined and fixed particular value or may be defined in every measurement by using data that is measured before a state of the fluid is changed. For example, in each measurement, a value of $S_{avg}(n)$ directly after the fluid is changed from a liquid to a gas, and a value of $S_{avg}(n)$ directly after the fluid is changed from a gas to a liquid may be used as the reference value $S_c$.

Alternatively, instead of using an average value, variation of the average value may be used, for example, by comparing a difference value with a reference value, the difference value being the difference between an average value of light intensity measured by the detecting unit over a first time frame and an average value of light intensity measured a predetermined number of times over a second time frame that is earlier than the first time frame. For example, in a case where a difference between an average value of optical signals that are most recently measured and an average value of optical signals that were previously measured is greater than a reference variation value, it is possible to determine whether the status of the fluid is changed. This method may be calculated by using Equation 2 below.

$$\Delta S_c \le |S_{avg}(n) - S_{avg}(n_0)| \quad \text{[Equation 2]}$$

In Equation 2 above, $S_{avg}(n)$ indicates an average value of $n_a$ pieces of data that are most recently measured, and $S_{avg}(n_0)$ indicates an average value of $n_a$ pieces of data that were measured over a predetermined number of times prior to the $S_{avg}(n)$. That is, if a difference between an average value of a plurality of pieces of data that are most recently measured and an average value of the plurality of pieces of data that were previously measured over a predetermined number of times is equal to or greater than a predetermined reference variation value ΔSc, it is possible to determine that the status of the fluid is changed.

Figure 8B:
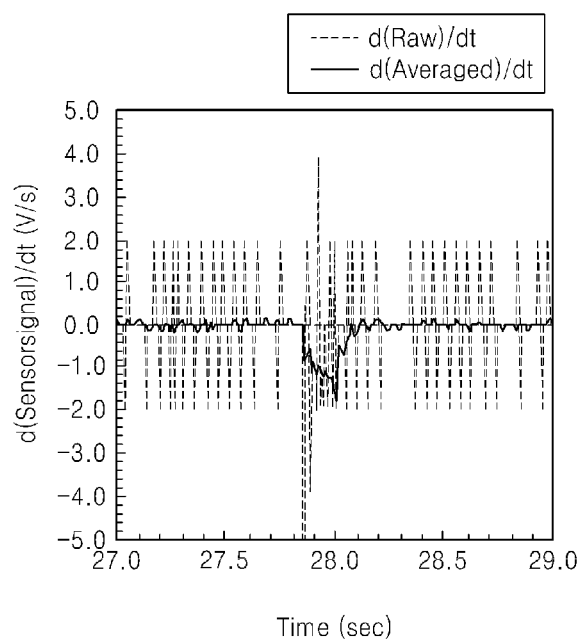

Alternatively, the determination may be performed by using values obtained by temporally differentiating a plurality of pieces of data, for example, by comparing a differential value with a reference value, wherein the differential value is the difference in the intensity of light reflected from the microfluidic device measured by the detecting unit at a first time point and the average intensity of the light reflected from the microfluidic device measured a predetermined number of times before the first time point. For example, in FIG. 8B, a graph denoted by a dotted line is obtained by temporally differentiating the graph of the original data shown in FIG. 8A, and a graph denoted by a solid line is obtained by temporally differentiating the graph of the average value shown in FIG. 8A. In the graph denoted by a dotted line, differential values significantly vary over time, and their variation values sharply increase at a moment when the state of the fluid is changed from a gas to a liquid. Also, in the graph denoted by a solid line, variation of differential values is very small while the state of the fluid is not changed. However, at a moment when the state of the fluid is changed from a gas to a liquid, the differential values are sharply and instantly changed. Thus, by comparing the variation of the differential values with a predetermined reference variation, it is possible to determine that the status of the fluid is changed. In particular, when the averaged data are differentiated, it is easier to determine a change in the state of the fluid. For example, the differentiation method may be calculated by using Equation 3 below.

$$\Delta S'_c \le \frac{|S_{avg}(n) - S_{avg}(n_0)|}{t_n - t_0} \quad \text{[Equation 3]}$$

In Equation 3, $t_n$ indicates a time at which $S_{avg}(n)$ is obtained, and $t_0$ indicates a time at which $S_{avg}(n_0)$ is obtained. That is, if a value is equal to or greater than a predetermined reference variation value $\Delta S'_c$, it is possible to determine that the status of the fluid is changed, wherein the value is obtained by dividing a difference between an average value of a plurality of pieces of data that are most recently measured and an average value of the plurality of pieces of data that are previously measured over a predetermined number of times, by a time.

Figure 9:
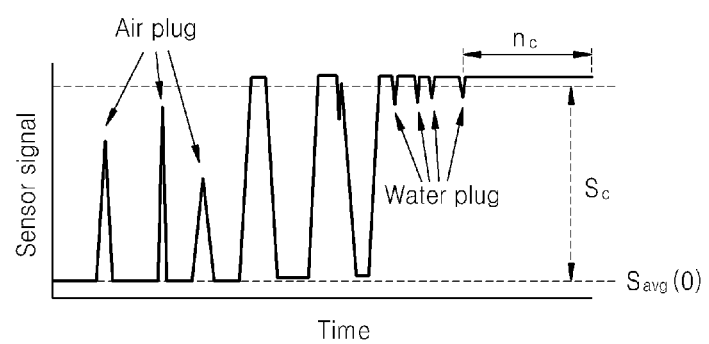
FIG. 9 is a graph illustrating an algorithm to prevent a wrong determination caused by bubbles in a liquid or droplets in a gas, according to an example embodiment.

In order to prevent a wrong determination that is caused when bubbles exist in a liquid or droplets exist in a gas, the determination regarding a change in the state of the fluid may be performed only when a predetermined number of cases in which data values are constantly greater than or equal to a predetermined reference value is maintained. For example, referring to FIG. 9, it is assumed that a fluid in the micro-channel 210 is initially in a liquid state, and then after a predetermined time period, as air enters the micro-channel 210, the fluid is changed to a gas state. An average data value with respect to initial optical signals that are measured before the inflow of the air is $S_{avg}(0)$. Afterward, when the air enters the micro-channel 210, an average value of the optical signals exceeds a reference value $S_c$. However, because a plurality of droplets exist in the micro-channel 210, data may be changed with respect to a reference value. Thus, while the data varies with respect to the reference value, it is not determined that a state of the fluid is changed, and when values of the optical signals or an average value of the optical signals, which are sequentially measured over a predetermined number of times $n_c$, is all equal to or greater than the reference value, it is possible to determine that the fluid in the micro-channel 210 is completely changed from a liquid to a gas. That is, when a signal indicating a change in the state of the fluid appears a predetermined number of times, it is possible to finally determine that the state of the fluid is changed.

The aforementioned methods of determining a change in a state of a fluid may be performed at only one measurement point of the microfluidic device 200 or may be performed while a plurality of measurement points are scanned. Also, in a case where the state of the fluid is monitored while the plurality of measurement points are scanned, the determination may be independently performed on each of the plurality of measurement points, or results of the determinations with respect to the plurality of measurement points may be colligated and then a final determination may be issued. For example, the fluid control apparatus 100 may move the light source 131 and the photodetector 132 to a measurement point of the microfluidic device 200 by using the transporting unit 120 and may monitor a state of a fluid, and then may move the light source 131 and the photodetector 132 to a next measurement point. Here, when the fluid control apparatus 100 detects a change in the state of the fluid in the measurement point, the fluid control apparatus 100 may determine that the state of the fluid is changed only in the measurement point. Alternatively, after a plurality of measurement points in a section in which a fluid flows are scanned, when the fluid control apparatus 100 detects a change in a state of the fluid in all of the plurality of measurement points, the fluid control apparatus 100 may determine that the state of the fluid in the section is changed.

Also, when a state of a fluid is monitored at a plurality of measurement points, one of the plurality of measurement points may be initially monitored during a predetermined time, and then a next one of the plurality of measurement points may be monitored. When the monitoring operation with respect to all of the plurality of measurement points is completed, the initial measurement point is monitored again, and here, a previous measurement result at the initial measurement point may be compared with a current measurement result at the initial measurement point, so that a state of a fluid at the initial measurement point may be determined.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A fluid control apparatus comprising:
   a detecting unit configured to irradiate light towards a microfluidic device, detect light reflected from the microfluidic device, and output a signal based on the light reflected from the microfluidic device;
   a transporting unit configured to move the detecting unit to a measurement position relative to the microfluidic device;
   a determining unit configured to control a transporting operation performed by the transporting unit, and determine a state of a fluid in the microfluidic device at the measurement position based on the signal output from the detecting unit; and
   a fluid control unit configured to control movement of the fluid in the microfluidic device based on the state of the fluid determined by the determining unit,
   wherein the determining unit determines whether the fluid in the microfluidic device at the measurement position is a liquid or a gas based on the intensity of the light reflected from the microfluidic device,
   wherein the determining unit determines the state of the fluid by comparing a differential value with a reference value, wherein the differential value is the difference in the intensity of light reflected from the microfluidic device measured by the detecting unit at a first time point and the average intensity of the light reflected from the microfluidic device measured a predetermined number of times before the first time point.

2. The fluid control apparatus of claim 1, wherein the detecting unit comprises a light source that irradiates light toward the microfluidic device and a photodetector that detects the light reflected from the microfluidic device.

3. The fluid control apparatus of claim 2, wherein the detecting unit further comprises a reflection plate positioned to reflect the light irradiated towards the microfluidic device that passes through the microfluidic device toward the photo detector.

4. The fluid control apparatus of claim 3, wherein the light source and the photodetector are disposed opposite the reflection plate relative to the microfluidic device.

5. The fluid control apparatus of claim 1, wherein the transporting unit comprises:
   a frame;
   a motor that is disposed at a side of the frame;
   a lead screw that is rotated by the motor,
   a mount that performs linear movement according to rotation of the lead screw; and
   a guide bar attached to the frame so as to guide movement of the mount.

6. The fluid control apparatus of claim 5, wherein the detecting unit comprises a light source that irradiates light toward the microfluidic device and a photodetector that detects the light reflected from the microfluidic device, wherein the light source and the photodetector are disposed at the mount.

7. The fluid control apparatus of claim 5, wherein the mount comprises a holder configured to slide on the guide bar to guide the movement of the mount.

8. The fluid control apparatus of claim 5, wherein the transporting unit further comprises one or more position sensors that are attached to the frame so as to detect a position of the mount while the mount moves.

9. The fluid control apparatus of claim 1, wherein the determining unit comprises:
   a sensor circuit for exchanging a signal with the detecting unit;
   a driving circuit for exchanging a signal with the transporting unit; and
   a control circuit that controls the detecting unit via the sensor circuit and controls the transporting unit via the driving circuit, wherein control software controls operations of the control circuit and determines a state of the fluid based on the signal from the detecting unit.

10. The fluid control apparatus of claim 1, wherein the determining unit determines the state of the fluid by comparing a value of the intensity of the light reflected from the microfluidic device with a reference value.

11. The fluid control apparatus of claim 1, wherein the determining unit determines the state of the fluid by comparing an average value of light intensities measured at two or more different time points to a reference value.

12. A fluid control apparatus comprising:
   a detecting unit configured to irradiate light towards a microfluidic device, detect light reflected from the microfluidic device, and output a signal based on the light reflected from the microfluidic device;
   a transporting unit configured to move the detecting unit to a measurement position relative to the microfluidic device;
   a determining unit configured to control a transporting operation performed by the transporting unit, and determine a state of a fluid in the microfluidic device at the measurement position based on the signal output from the detecting unit; and
   a fluid control unit configured to control movement of the fluid in the microfluidic device based on the state of the fluid determined by the determining unit,
   wherein the determining unit determines whether the fluid in the microfluidic device at the measurement position is a liquid or a gas based on the intensity of the light reflected from the microfluidic device, wherein the determining unit determines the state of the fluid by comparing a difference value with a reference value, wherein the difference value is the difference between an average value of light intensity measured by the detecting unit over a first time frame and an average value of light intensity measured a predetermined number of times over a second time frame that is earlier than the first time frame.

13. A fluid control apparatus comprising:
   a detecting unit configured to irradiate light towards a microfluidic device, detect light reflected from the microfluidic device, and output a signal based on the light reflected from the microfluidic device;
   a transporting unit configured to move the detecting unit to a measurement position relative to the microfluidic device;
   a determining unit configured to control a transporting operation performed by the transporting unit, and determine a state of a fluid in the microfluidic device at the measurement position based on the signal output from the detecting unit; and
   a fluid control unit configured to control movement of the fluid in the microfluidic device based on the state of the fluid determined by the determining unit,
   wherein the determining unit determines whether the fluid in the microfluidic device at the measurement position is a liquid or a gas based on the intensity of the light reflected from the microfluidic device, wherein the determining unit determines the state of the fluid by comparing a differential value with a reference value, wherein the differential value is the difference in the intensity of light reflected from the microfluidic device measured by the detecting unit at a first time point and the average intensity of the light reflected from the microfluidic device measured a predetermined number of times before the first time point.

14. The fluid control apparatus of claim 10, wherein the determining unit determines a change in the state of the fluid at the measurement position based on a predetermined number of signals indicating a change in light intensity reflected from the microfluidic device.

15. A method of controlling a fluid, the method comprising:
   moving a light source and a photodetector to a measurement position relative to a microfluidic device;
   irradiating light towards the microfluidic device;
   measuring an intensity of light reflected from the microfluidic device;
   determining whether a state of a fluid in the microtluidic device is changed from a gas state to a liquid state or is changed from a liquid state to a gas state based on a change in the measured intensity of the light reflected from the microfluidic device; and
   controlling movement of the fluid in the microfluidic device based on the state of the fluid in the microfluidic device,
   wherein determining the state of the fluid comprises comparing a differential value with a reference value, wherein the differential value is the difference between a first average value of light intensity over a given time frame and a second average value of light intensity measured a predetermined number of times prior to the given time frame.

16. The method of claim 15, wherein determining the state of the fluid comprises comparing the measured intensity of the light reflected from the microfluidic device with a reference value.

17. The method of claim 15, wherein determining the state of the fluid comprises comparing an average value of light intensities measured at two or more different time points to a reference value.

18. A method of controlling a fluid, the method comprising:
   moving a light source and a photodetector to a measurement position relative to a microfluidic device;
   irradiating light towards the microfluidic device;
   measuring an intensity of light reflected from the microfluidic device;
   determining whether a state of a fluid in the microfluidic device is changed from a gas state to a liquid state or is changed from a liquid state to a gas state based on a change in the measured intensity of the light reflected from the microfluidic device; and
   controlling movement of the fluid in the microfluidic device based on the state of the fluid in the microfluidic device, wherein determining the state of the fluid comprises comparing a difference value with a reference value, wherein the difference value is the difference between an average value of light intensity measured by the detecting unit over a first time frame and an average value of light intensity measured a predetermined number of times over a second time frame that is earlier than the first time frame.

19. The method of claim 16, wherein determining the state of the fluid comprises determining a change in the state of the fluid at the measurement position based on a predetermined number of signals indicating a change in light intensity reflected from the microfluidic device.

20. The method of claim 15, further comprising moving the light source and the photodetector to a second measurement position after monitoring the state of the fluid at a first measurement position.

21. The method of claim 20, wherein determining the state of the fluid comprises determining that the state of the fluid at the first measurement position is different than the state of the fluid at the second measurement position.

22. The method of claim 20, wherein the method comprises monitoring the state of the fluid at each of a plurality of measurement points in a section in which the fluid flows, and determining that the state of the fluid in the section is changed.

23. The method of claim 20, further comprising monitoring a state of a fluid at a first measurement point and monitoring of the state of the fluid at a plurality of additional measurement points, and determining the state of the fluid at the first measurement point by comparing the light intensity reflected from the microfluidic device at the first measurement point with the light intensity reflected from the microfluidic device at one or more of the plurality of additional measurement points.

24. The fluid control apparatus of claim 1, wherein the detecting unit is configured to detect a change in the fluid state at the measurement position from gas to liquid or liquid to gas based on a change in the intensity of the light reflected from the microfluidic device.

* * * * *